United States Patent [19]

Edwards, Jr.

[11] Patent Number: 5,154,925
[45] Date of Patent: Oct. 13, 1992

[54] TREATMENT OF TIBIAL DYSCHONDROPLASIA

[75] Inventor: Hardy M. Edwards, Jr., Winterville, Ga.

[73] Assignee: University of Georgia Research Foundation, Inc., Athens, Ga.

[21] Appl. No.: 630,748

[22] Filed: Dec. 20, 1990

Related U.S. Application Data

[63] Continuation of Ser. No. 311,540, Feb. 16, 1989, abandoned.

[51] Int. Cl.⁵ ............................................ A61K 31/59
[52] U.S. Cl. ............................................ 424/422; 424/8; 424/426; 424/442; 424/451; 424/457; 424/456; 424/464; 424/489; 424/490; 424/494; 514/167
[58] Field of Search .................. 424/442, 422, 426; 514/167

[56] References Cited

U.S. PATENT DOCUMENTS

| | | | |
|---|---|---|---|
| 3,565,924 | 2/1971 | DeLuca et al. | 260/397.2 |
| 3,697,559 | 10/1972 | DeLuca et al. | 260/397.2 |
| 3,741,996 | 6/1973 | DeLuca et al. | 260/397.2 |
| 3,847,955 | 11/1974 | DeLuca | 260/397.2 |
| 3,880,894 | 4/1975 | DeLuca et al. | 260/397.2 |
| 4,012,509 | 3/1977 | Frank | 514/167 |
| 4,110,446 | 8/1978 | DeLuca et al. | 424/236 |
| 4,119,647 | 10/1978 | Liebman et al. | 260/397.2 |
| 4,201,881 | 5/1980 | DeLuca et al. | 568/819 |
| 4,217,288 | 8/1980 | DeLuca et al. | 260/397.2 |
| 4,224,231 | 9/1980 | DeLuca | 260/397.2 |
| 4,225,596 | 9/1980 | DeLuca | 424/236 |
| 4,226,788 | 10/1980 | DeLuca et al. | 260/397.2 |
| 4,229,359 | 10/1980 | DeLuca et al. | 260/397.2 |
| 4,254,045 | 3/1981 | DeLuca et al. | 260/397.2 |
| 4,292,250 | 9/1981 | DeLuca et al. | 260/397.2 |
| 4,305,880 | 12/1981 | DeLuca et al. | 260/397.1 |
| 4,307,231 | 12/1981 | DeLuca et al. | 542/428 |
| 4,310,467 | 1/1982 | Batcho et al. | 260/397.5 |
| 4,310,522 | 1/1982 | Frank | 424/236 |
| 4,336,193 | 6/1982 | DeLuca et al. | 260/239.57 |
| 4,338,312 | 7/1982 | DeLuca et al. | 424/236 |
| 4,358,406 | 11/1982 | DeLuca et al. | 260/239.55 R |
| 4,364,941 | 12/1982 | Kiyoki | 514/167 |
| 4,411,833 | 10/1983 | DeLuca et al. | 260/239.55 R |
| 4,421,690 | 12/1983 | Partridge et al. | 260/397.1 |
| 4,495,181 | 1/1985 | Norman et al. | 514/167 |
| 4,502,991 | 3/1985 | DeLuca et al. | 260/397.2 |
| 4,552,698 | 11/1985 | DeLuca et al. | 260/397.2 |
| 4,594,432 | 6/1986 | Baggiolini et al. | 549/214 |
| 4,612,308 | 9/1986 | Baggiolini et al. | 514/167 |
| 4,613,594 | 9/1986 | Baggiolini et al. | 514/167 |
| 4,617,297 | 10/1986 | Boris et al. | 514/167 |
| 4,619,920 | 10/1986 | DeLuca et al. | 514/167 |
| 4,711,881 | 12/1987 | Ikekawa | 514/167 |
| 4,761,406 | 8/1988 | Flora et al. | 514/86 |

OTHER PUBLICATIONS

Boris et al., *J. Nutr.* 107, 194 (1977).
Edwards et al., *J. Nutr.* 113, 1568 (1983).
Edwards, *J. Nutr.* 114, 1001 (1984).
Edwards, *J. Nutr.* 117, 964 (1987).
Ghazarian et al., *J. Biol. Chem.* 249(19), 3026 (1974).
Hesse et al., *J. Am. Chem. Soc.* 95(8), 2748 (1973).
Holick et al., *Biochemistry* 10(14), 2799 (1971).
Leach et al., *J. Nutr.* 102, 1673 (1972).
McNutt et al., *J. Nutr.* 103, 681 (1973).
Mongin et al., *Growth and Poultry Meat Production*, 235-247 (1977).
Norman et al., *J. Nutr.* 102, 1709 (1972).
Sauveur et al., *XV World Poultry Congress*.
Semmler et al., *Tet. Let.* 40, 4147 (1972).
Shiuey et al., *J. Org. Chem.* 53(5), 1040 (1988).
Stevens et al., *Poult. Sci.* 63, 765 (1984).
Suso et al., *Poult. Sci.* 47: 991-999 (1968).
Yoon et al., *Archives of Biochem. and Biophysics* 203(2), 529 (1980).
Zemaitis et al., *Biochem. Pharmacol.* 25, 1355 (1976).

*Primary Examiner*—Thurman K. Page
*Assistant Examiner*—James M. Spear
*Attorney, Agent, or Firm*—Kilpatrick & Cody

[57] ABSTRACT

A method and compositions to treat and prevent tibial dyschondroplasia in animals, particularly fowl, which includes administering to animals an effective amount of the vitamin $D_3$ derivatives 1,25-dihydroxycholecalciferol, 1,25-dihydroxy-26,27-hexadeuterocholecalciferol, 1-hydroxycholecalciferol, 1,24,25-trihydroxycholecalciferol, 1,25-dihydroxy-24-fluorocholecalciferol, or 25-hydroxycholecalciferol alone or in combination with an effective amount of vitamin $D_3$. The vitamin $D_3$ derivatives can be administered orally, subcutaneously, intramuscularly, intravenously or intraperitoneally.

19 Claims, 1 Drawing Sheet

TREATMENT OF TIBIAL DYSCHONDROPLASIA

This is a continuation of Ser. No. 07/311,540 filed Feb. 16, 1989, now abandoned.

BACKGROUND OF THE INVENTION

This invention relates to the field of veterinary science, and is in particular a method for reducing the incidence of tibial dyschondroplasia in animals.

The federal government has rights in this invention by virtue of the fact that it partially funded the experimentation which lead to the discovery of this invention.

Tibial dyschondroplasia is a skeletal abnormality which occurs in rapidly growing animals such as broiler chickens or turkeys. The abnormality is characterized by an unmineralized, unvascularized mass of cartilage located in the proximal ends of the tibiotarsus and the tarsusmetatarsus. The cartilage extends from the growth plate into the metaphysis. In fowl, tibial dyschondroplasia usually appears between three and eight weeks of age.

In some chickens and turkeys, the prehypertrophic cartilage persists into adulthood and is restricted to the posterior medial portion of the proximal tibiotarsal bone, and the birds remain clinically normal. An incidence of 10 to 30% of birds with subclinical dyschondroplasia is common in many flocks. In the more severe cases of tibial dyschondroplasia, the abnormal tissue occupies the whole metaphysis of the proximal tibiotarsal bone and also develops in the proximal tarsometatarsal bone. Birds with these more severe lesions may be lame, with bowing of the affected bones. These chickens can have difficulty walking and are prone to falling down, causing injury and decreasing growth rate. The disease also increases the death rate of animals during the growth period. Further, many of the birds suffering from the disease develop breast blisters and leg deformities that result in hemorrhages.

Tibial dyschondroplasia increases the percentage of carcasses downgraded or condemned in processing plants, which results in decreased profits for the processor. When flocks of birds have a high incidence of tibial dyschondroplasia, the crooked legs can interfere with the shackling of the fowl during processing and can actually cause mechanical problems in operating the processing line where the slaughtered fowl are conveyed on machines which handle the birds by their legs. Fowl with tibial dyschondroplasia have insufficient leg strength to be carried in this manner.

A number of studies have been conducted to determine both the cause of dyschondroplasia and a method for treatment or prevention. Leach and Nesheim, "Further Studies on Tibial Dyschondroplasia Cartilage Abnormality in Young Chicks", *J. Nutr.* 102, 1673 (1972), indicated that the cartilage abnormality is a result of an inherited physiological defect, the expression of which is under dietary control. They were not able to determine the nutritional factors responsible for expression. However, they found that manipulations of the mineral mixture that resulted in changes in acid/base or cation/anion balance in the chick altered the incidence of abnormality. In particular, high chloride level in the diet increased the incidence of the abnormality when chicks were fed diets similar to those used commercially.

Mongin and Sauveur, in "Interrelationship Between Mineral Nutrition, Acid-Based Balance, Growth and Cartilage Abnormalities," *Growth and Poultry Meat Production,* Borman, K. N. and Wilson, B. J., Eds., pp. 235-247, British Poultry Science Ltd., Edinburgh, Scotland (1977), hypothesized that the metabolic acidosis in chickens fed high dietary chloride levels caused tibial dyschondroplasia because of impaired bone mineralization resulting from alteration of vitamin D metabolism.

Chickens made acidotic by administration of ammonium chloride show reduced conversion of $25(OH)D_3$ to $1,25(OH)_2D_3$, although the production of 24,25-dihydroxycholecalciferol ($24,25(OH)_2D_3$) from $25(OH)D_3$ was not consistently affected by acidosis, as also reported by Sauveur and Mongin, in "Influence of Dietary Level of Chloride, Sodium and Potassium on Chick Cartilage Abnormalities," Proceedings of XV World Poultry Congress, pp. 180-181 (1977).

However, supplementation of chickens with 20 ng/day of either 1,25-dihydroxycholecalciferol ($1,25(OH)_2D_3$) or 24,25-dihydroxycholecalciferol ($24,25(OH)_2D_3$) was demonstrated to have no effect on the incidence of tibial dyschondroplasia, as described by Edwards in "Studies on the Etiology of Tibial Dyschondroplasia in Chickens", *J. Nutr.,* 114, 1001 (1984).

Calcium and phosphorus levels in the diet have been found to be major nutritional factors influencing the expression of tibial dyschondroplasia. High calcium in the feed retards the development of the lesion, whereas high phosphorus levels appear to accentuate the development of the lesions, as reported by Edwards and Veltmann, "The Role of Calcium and Phosphorus in the Etiology of Tibial Dyschondroplasia in Young Chicks," *J. Nutr.,* 113, 1568 (1983).

Increases in the magnesium content of the chick diet decrease the incidence of tibial dyschondroplasia; however, the effect of magnesium is not as strong as that of calcium, as demonstrated by Edwards, "Studies on the Etiology of Tibial Dyschondroplasia in Chickens", *J. Nutr.,* 114, 1001 (1984).

Given the large economic loss to meat producers caused by animals afflicted with tibial dyschondroplasia as well as the discomfort of the afflicted animal and the resulting unsanitary conditions caused by the diseased dysfunctional animal, it would be of great benefit to find an effective method and compositions to reduce the incidence of this disease.

It is therefore an object of the present invention to provide a method and compositions for the treatment and prevention of tibial dyschondroplasia in animals.

It is another object of the present invention to provide compositions which may be administered economically and easily to animals to reduce the incidence of tibial dyschondroplasia.

SUMMARY OF THE INVENTION

The objects of the present invention described above are achieved with a method and compositions for the treatment and prevention of tibial dyschondroplasia in animals, particularly fowl.

The method includes administering to animals a composition delivering an effective amount of 1,25-dihydroxycholecalciferol, 1,25-dihydroxy-26,27-hexadeuterocholecalciferol, 1-hydroxycholecalciferol, 1,24,25-trihydroxycholecalciferol, 1,25-dihydroxy-24-fluorocholecalciferol, 25-hydroxycholecalciferol, or combinations thereof, in a pharmaceutically acceptable carrier.

These compositions may be administered to animals orally, subcutaneously, intramuscularly, intravenously or intraperitoneally. For example, it may be given in a feed composition, the water supply, by time or slow-release bolus or other controlled drug delivery device, an orally administered capsule, or by an injection.

The effectiveness of the method of the present invention in reducing the incidence of tibial dyschondroplasia, can be enhanced by administering the vitamin $D_3$ derivatives in combination with an effective amount of vitamin $D_3$.

In the preferred embodiment for prevention of tibial dyschondroplasia in poultry, a composition is administered which delivers a dosage of between approximately 0.1 and 20 micrograms of vitamin $D_3$ derivative per day. The administration preferably is initiated on the first day of life and is continued for at least three weeks.

Tibial dyschondroplasia already established in poultry can be treated according to the method of the present invention by administering a composition which delivers a dosage of between 0.1 and 20 micrograms per day. The treatment is initiated as soon as the disease is discovered and continued until cured.

In the preferred embodiment for prevention or treatment of tibial dyschondroplasia in other animals, a composition is administered which delivers a dosage of at least 1 microgram per day per kilogram of weight. The treatment should be initiated at birth and continued throughout the animal's rapid growth stage.

DETAILED DESCRIPTION OF THE INVENTION

Figure 1:
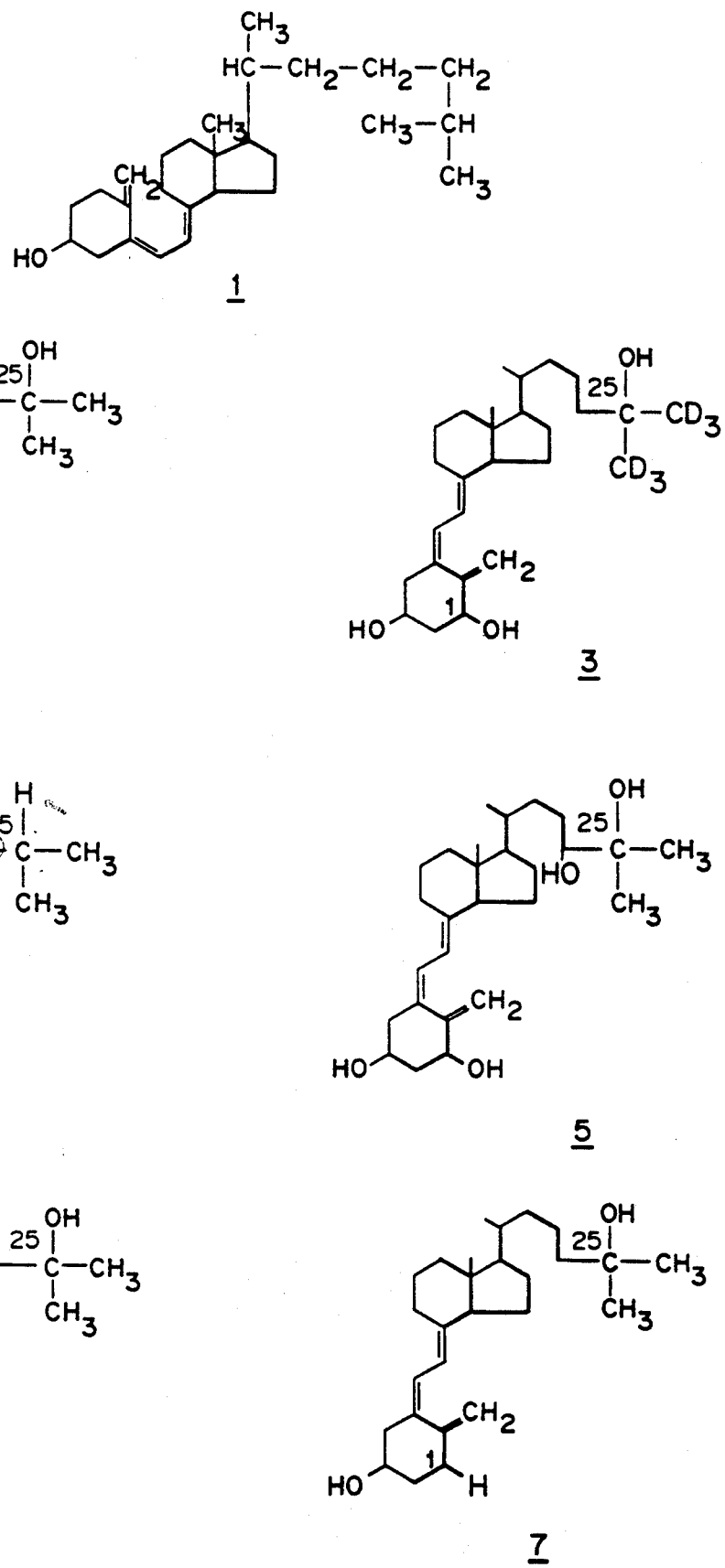
FIG. 1 is an illustration of the chemical structures of vitamin $D_3$ (cholecalciferol) (1), 1,25-dihydroxycholecalciferol (2), 1,25-dihydroxy-26,27-hexadeuterocholecalciferol (3), 1-hydroxycholecalciferol (4), 1,24,25-trihydroxycholecalciferol (5), 1,25-dihydroxy-24-fluorocholecalciferol (6), and 25-hydroxycholecalciferol (7), as used in the method and compositions of the present invention.

The present invention is a method and compositions to treat and prevent tibial dyschondroplasia in animals. Reduction in the incidence of tibial dyschondroplasia improves the health of the animals treated and the sanitary conditions of the animal facility. It also allows more chickens and turkeys to be successfully processed before and after slaughter, thereby reducing costs to the processor.

Referring to FIG. 1, the method includes administering to animals a composition which delivers an effective amount of the vitamin $D_3$ derivative 1,25-dihydroxycholecalciferol (2), 1,25-dihydroxy-26,27-hexadeuterocholecalciferol (3), 1-hydroxycholecalciferol (4), 1,24,25-trihydroxycholecalciferol (5), 1,25-dihydroxy-24-fluorocholecalciferol (6), or 25-hydroxycholecalciferol (7) to reduce or reverse the development of abnormal cartilage at the proximal end of the tibia.

Although described with specific reference to chickens and turkeys, the method and compositions are equally effective in the treatment of other types of animals, including but not limited to pheasant, ducks, swine, dogs, rabbits, cattle, and fish. For example, Great Danes have a particular problem with tibial dyschondroplasia due to their rapid growth. Administration of the above described compositions according to the method described here should be efficacious in reducing the incidence of the disease in these animals.

Effective Dosage Range

In contrast to the previous reports by Edwards in "Studies on the Etiology of Tibial Dyschondroplasia in Chickens", *J. Nutr.*, 114, 1001 (1984), that administration to chickens of 20 ng/day of either 1,25-dihydroxycholecalciferol (1,25(OH)$_2$D$_3$) or 24,25-dihydroxycholecalciferol (24,25(OH)$_2$D$_3$) has no effect on the incidence of tibial dyschondroplasia, it has now been discovered that administration to chickens of certain vitamin $D_3$ derivatives in a dosage range of between approximately 0.1-20 g of vitamin $D_3$ derivative per day from one day old to three weeks of age causes a significant reduction of the incidence of tibial dyschondroplasia.

In particular, the incidence of tibial dyschondroplasia in fowl can be lowered by administering daily dosages of vitamin $D_3$ compound in the range of about 0.2 micrograms ($\mu$g) per day per bird for a 1 week old bird to about 2 g per day per bird for an 8 week old bird.

An effective dosage for prevention of tibial dyschondroplasia in animals other than fowl is at least 1 microgram of vitamin $D_3$ derivative per day per kilogram of body weight. This dosage results in normal calcification and shaping of bones as well as preventing the disease. The treatment should preferably be started at birth and continued throughout the period of rapid growth. It can be continued for the life of the animal. For example, in poultry, treatment is preferably begun at one day of age, and continued for at least three to four weeks.

Administration of the vitamin $D_3$ derivatives of the present invention later than one day of age will still provide a therapeutic effect, but will be slightly less effective at preventing the onset of the disease.

The compositions of the present invention can also be administered as a treatment for tibial dyschondroplasia already established in the animal. The same dosages are used as for prevention of the disease. The administration of the compositions should begin as soon as the disease is discovered, and continued until the animal is cured. However, administration of the compositions will not reverse the abnormal shape of bones caused by the disease.

The effectiveness of administration of the compositions of the present invention on prevention or treatment of tibial dyschondroplasia in fowl can be determined by making a longitudinal cut across the tibia and inspecting for incidence and severity of the disease, as described in the Example of Treatment of Tibial Dyschondroplasia.

The effectiveness of administration of the compositions delivering the vitamin $D_3$ derivatives on prevention or treatment of dyschondroplasia in other animals can be determined by internal inspection of the bone for abnormal cartilage development or external inspection of bone for irregularities, bowed shape, or weakness.

Method for Administration

For poultry, a suitable and easy means of administration of the compounds of the present invention is to include them in bird feed at a dosage range of between approximately 5 and 20 micrograms per kilogram of bird feed. A starter feed given to chickens in the first two weeks of life can be mixed with the vitamin $D_3$ derivative at a ratio of 10-20 $\mu$g of compound per kg of feed. The grower feed given to chickens in the next two weeks of life may contain 5-10 $\mu$g of compound per kg of feed and the finisher feed given to chickens in their last weeks of life may contain up to 5 g of compound per kg of feed. The amount of compound in the feed is decreased over time to take into account the increased feed intake of the animal as it grows. This allows the producer to use cheaper feed for the older bird.

Vitamin $D_3$ in Combination with Vitamin $D_3$ Derivatives 1,25-Dihydroxycholecalciferol (2), 1,25-dihydroxy-26,27-hexadeuterocholecalciferol (3), 1-hydroxycholecalciferol (4), 1,24,25-trihydroxycholecalciferol (5), 1,25-dihydroxy-24-fluorocholecalciferol (6) or 25-hydroxycholecalciferol (7), can be administered in combination with vitamin $D_3$ to insure a healthy animal. Animals, including poultry, should normally be given adequate vitamin $D_3$ in their basal diet. Vitamin $D_3$ aids normal calcium transport and metabolism. Vitamin $D_3$ is also somewhat effective in preventing the development of tibial dyschondroplasia. As seen in Tables 3 and 4, however, chickens given a basal diet which includes 1100 ICU of vitamin $D_3$ still have a high incidence of tibial dyschondroplasia (Study 1, 42% incidence; Study 2, 39%; Study 3, 18%; Study 4, 35%). Administration of additional vitamin $D_3$ to the chickens' diet in some cases slightly reduces the incidence of the disease (Study 1, 26% incidence; Study 2, 31%), and in some cases does not effect the incidence of the disease at all (Study 3, 22% incidence; Study 4, 35%). However, administration of 10 μg of the vitamin $D_3$ derivative per day to chickens which are supplied vitamin $D_3$ in their basal diet produces a significant decrease in the incidence of the disease (Study 3, 9–12% incidence; Study 4, 8–16% incidence).

The amount of vitamin $D_3$ found effective to cause a reduction in the incidence of tibial dyschondroplasia is in the range of 0.5 to 2 μg per kilogram of body weight of animal per day.

Poultry fed a basal diet which contains dietary vitamin $D_3$ and an effective amount of a vitamin $D_3$ derivative will have a lower incidence of tibial dyschondroplasia than those fed an effective amount of the vitamin $D_3$ derivative alone, as seen in Table 1.

TABLE 1

| $D_3$ ICU/kg diet | 1,25(OH)$_2$D$_3$ μg/kg diet | 16-d wt g | Gain/feed | Bone ash % | Ricket incidence % | Tibial dyschondroplasia Incidence % | Score | % #3 | #3/total |
|---|---|---|---|---|---|---|---|---|---|
| 0 | 0 | 345 | .667 | 34.3 | 37 | 87 | 1.4 | 17 | 5/30 |
| 0 | .1 | 343 | .652 | 34.0 | 70 | 76 | 1.3 | 11 | 3/29 |
| 0 | 1 | 344 | .641 | 35.3 | 33 | 78 | 1.2 | 12 | 3/28 |
| 0 | 10 | 350 | .621 | 38.7 | 0 | 0 | 0$^e$ | 0 | 0/29 |
| 1100 | 0 | 329 | .626 | 35.7 | 24 | 59 | 0.9 | 7 | 2/29 |
| 1100 | .1 | 349 | .630 | 36.3 | 27 | 63 | 1.0 | 7 | 2/30 |
| 1100 | 1 | 356 | .685 | 36.3 | 7 | 37 | 0.5 | 3 | 1/30 |
| 1100 | 10 | 348 | .609 | 39.0 | 0 | 18 | 0.2 | 0 | 0/28 |

It is clear that the vitamin $D_3$ derivatives are not mere substitutes for vitamin $D_3$, but are performing a biological role separate from and in addition to that of vitamin $D_3$.

Administration of Combinations of Vitamin $D_3$ Derivatives

Another embodiment of the present invention includes administering the vitamin $D_3$ derivatives in combination, with or without Vitamin $D_3$. For example, a composition delivering a dosage of a 0.1–20 g of a combination of the vitamin $D_3$ derivatives per day to poultry is efficacious in treating and preventing tibial dyschondroplasia. Any of the compounds of the present invention may be administered in such composition combinations.

Preparation of Compositions to Treat Tibial Dyschondroplasia

The compositions of the present invention may be administered to the animals orally, subcutaneously, intramuscularly, intravenously or intraperitoneally. For example, it may be given in a feed composition, the water supply, by injection, or by a controlled drug delivery device such as a time or slow release bolus, a microsphere, a microcapsule, or an orally administered capsule which can be time released.

Biodegradable, biocompatible implants are presently in use for controlled drug delivery in humans and animals. Acceptable materials for the delivery matrix include cellulose, gelatin, polylactides, polyglycolides, polyanhydrides, polyorthoesters, polyethylene vinyl acetate, and other polymers which degrade hydrolytically or enzymatically once implanted. The vitamin $D_3$ derivatives of the present invention can be incorporated into microspheres or microcapsules of these materials or other materials known to those of skill in the art. The microspheres or microcapsules are then implanted into the animal for release of the drug over time.

Suitable pharmaceutically acceptable carriers for veterinary drug delivery are known to those of skill in the art, and include saline, PBS (phosphate-buffered saline) and propylene glycol.

In the preferred dietary composition for the treatment of tibial dyschondroplasia in fowl, an effective amount of 1,25-dihydroxycholecalciferol (1), 1,25-dihydroxy-26,27-hexadeuterocholecalciferol (2), 1-hydroxycholecalciferol (4), 1,24,25-trihydroxycholecalciferol (5), 1,25-dihydroxy-24-fluorocholecalciferol (6) or 25-hydroxycholecalciferol (7, or a combination thereof, is provided in combination with sources of energy such as corn, fat and soybean meal; sources of protein such as corn and soybean meal; amino acids such as DL-methionine; mineral sources such as iodized sodium chloride, a trace mineral mixture, selenium concentrate (0.02% sodium selenite), a phosphorus source such as dicalcium phosphate, a calcium source such as dicalcium phosphate and limestone and a vitamin mixture.

The vitamin mixture provides in milligrams/kilogram of diet (except as noted) vitamin A (as all-trans-retinyl acetate), 5,500 IU; vitamin $D_3$ (cholecalciferol), 1100 ICU or 27.5 μg; vitamin E (all-rac-α-tocopheryl acetate), 11 IU; riboflavin, 4.4; calcium pantothenate, 12; nicotinic acid, 44; choline Cl, 220; vitamin $B_{12}$, 9; vitamin $B_6$, 3.0; menadione (as menadione sodium bisulfite), 1.1; thiamin (as thiamin mononitrate) 2.2; folic acid, 3; biotin, 0.3; and ethoxyquin, 125.

The trace mineral mixture provides in milligrams/kilogram of diet $MnO_2$, 222; ZnO, 150, $FeSO_4 \cdot H_2O$, 200; $FeCO_3$, 83; $C_2SO_4$, 29; and $Ca(IO_3)_2$, 15.

A supplemented chicken feed, to which the compounds of the present invention may be added in above described dosages, is given in Table 2.

TABLE 2

| Composition of the basal diet. | |
|---|---|
| Ingredients | Amounts % |
| Ground yellow corn | 56.81 |
| Soybean meal (dehulled) | 35.00 |
| Poultry fat (stabilized) | 5.00 |
| Iodized sodium chloride | 0.45 |
| D,L-Methionine (98%) | 0.20 |
| Vitamin premix (as described above) | 0.25 |
| Trace mineral premix (as described above) | 0.10 |
| Se concentrate (0.02% from sodium selenite) | 0.05 |
| Dicalcium phosphate (feed grade) | 1.86 |
| Limestone | 0.28 |

The active compounds of the present invention can also be administered in combination with other commercially formulated or similar feeds.

Chickens fed the diet described in Table 2, without the vitamin $D_3$ derivatives of the present invention, will have a higher than normal incidence of tibial dyschondroplasia even though the diet contains a high level of vitamin $D_3$, because the diet has a high level of chloride and phosphorus and a low level of calcium (average analyzed values Cl 0.32%, P 0.76%, Ca 0.75%).

The compounds of the present invention are efficacious in a feed having any calcium composition, particularly those with a calcium composition of less than 2.5% by weight. Broiler chickens are typically fed a diet which has a range of calcium of 0.7 to 1.4% by weight, while egg laying hens are fed a diet with a higher calcium level.

A control system to test the effect of the vitamin $D_3$ derivatives on the incidence of tibial dyschondroplasia in fowl was developed using disulfiram [bis(diethylthiocarbamyl)disulfide], an alcohol deterrent, in a dietary dosage of approximately 30 mg/kg feed per day. Disulfiram supplementation lowers the absorption of calcium when given as an oral dose compared to controls. It is known that thiruram [bis(dimethylthiocarbamyl)disulfide], a compound used as a fungicide and bactericide which is structurally close to disulfiram and which also causes tibial dyschondroplasia, causes a rapid loss of intramuscularly injected calcium immediately after dosing. This suggests that calcium in the blood and soft tissues (gastrointestinal tract) can be lost more easily from the birds receiving thiruram or disulfiram but that once the calcium goes into the bone both thiruram and disulfiram have little effect on turnover.

Example of Treatment of Tibial Dyschondroplasia with Vitamin $D_3$ Derivatives

The effectiveness of 1,25-dihydroxycholecalciferol (2), 1,25-dihydroxy-26,27-hexadeuterocholecalciferol (3), 1-hydroxycholecalciferol (4), 1,24,25-trihydroxycholecalciferol (5), and 1,25-dihydroxy-24-fluorocholecalciferol (6) in reducing the incidence of tibial dyschondroplasia in chickens has been demonstrated using the following experimental procedure.

Newly hatched Peterson X Arbor Acre cockerels obtained from a commercial hatchery were used. The chickens were kept in electrically heated Petersime battery brooders with wire mesh floors located in a room in which the temperature was maintained at 22° C.; fluorescent lights were on 24 hours each day in the room and the cages, and sunlight was present during the day from large windows. There was no attempt to limit the natural production of Vitamin $D_3$. Ten birds were placed in each section of the Petersime batteries used at the start of the experiment. Food and water were always available to the chickens. The basal diet used is as described in Table 2. Disulfiram was added to the basal diet of some chickens as indicated in Table 4 at a level of 30 milligrams/kilogram of feed. Vitamin $D_3$ and its metabolites were added as indicated in Tables 3 and 4 to the diet at the following levels: Vitamin $D_3$, 27.5 micrograms per kilogram of feed (1100 ICU/kilogram); 1,25-dihydroxycholecalciferol (2), 1,25-dihydroxy-26,27-hexadeuterocholecalciferol (3), 1-hydroxycholecalciferol (4), 1,24(R),25-trihydroxycholecalciferol (5), 1,25-dihydroxy-24(R)-fluorocholecalciferol (6), and 25-hydroxycholecalciferol (7) at 10 g/kg.

TABLE 3

| | Study 1 | | | | | |
|---|---|---|---|---|---|---|
| | 16 Day wts. | | Bone ash | Tibial Dyschondroplasia | | |
| Treatments | g. | G:F | % | Incidence % | Score | #3/total |
| Basal | 416 | .696 | 40.6 | 42 | 2.77 | 10/30 |
| Basal + $D_3$ | 451 | .734 | 40.4 | 26 | 2.38 | 4/27 |
| Basal + 25OH$D_3$ | 395 | .667 | 40.2 | 17 | 1.50 | 1/28 |
| Basal + 1,25(OH)$_2D_3$ | 421 | .670 | 42.5 | 13 | 1.75 | 1/29 |
| Disulfiram | 433 | .750 | 39.9 | 70 | 2.71 | 16/30 |
| Disulfiram + $D_3$ | 432 | .708 | 40.0 | 40 | 2.80 | 9/27 |
| Disulfiram + 25OH$D_3$ | 398 | .706 | 39.7 | 58 | 2.54 | 11/30 |
| Disulfiram + 1,25(OH)$_2D_3$ | 426 | .701 | 41.9 | 23 | 2.33 | 4/30 |
| Means ± SEM | 420 ± 13 | .704.032 | 40.6 ± .2 | 36 ± 9 | 2.11 ± .48 | |

| | Study 2 | | | | | | | |
|---|---|---|---|---|---|---|---|---|
| | 16 Day wts. | | Bone ash | Tibial Dyschondroplasia | | | $^{47}$Ca | |
| Treatments | g | G:F | % | Incidence % | Score | #3/total | Intercept | Slope |
| Basal | 375 | .707 | 40.5 | 39 | 1.94 | 6/29 | 72 | −1.60 |
| Basal + $D_3$ | 368 | .647 | 40.5 | 31 | 2.47 | 5/29 | 77 | −1.88 |
| Basal + 25OH$D_3$ | 392 | .713 | 40.6 | 27 | 2.78 | 7/30 | 72 | −1.59 |
| Basal + 1,25(OH)$_2D_3$ | 361 | .661 | 42.2 | 13 | 2.17 | 2/30 | 84 | −2.85 |
| Disulfiram | 394 | .671 | 40.3 | 65 | 2.76 | 14/28 | 73 | −1.59 |
| Disulfiram + $D_3$ | 374 | .666 | 40.3 | 51 | 2.74 | 12/30 | 72 | −1.97 |
| Disulfiram + 25OH$D_3$ | 395 | .728 | 40.5 | 49 | 2.76 | 11/28 | 74 | −1.67 |

TABLE 3-continued

| | | | | | | | | |
|---|---|---|---|---|---|---|---|---|
| Disulfiram + 1,25(OH)₂D₃ | 377 | .684 | 42.0 | 30 | 2.44 | 6/30 | 79 | −2.11 |
| Means ± SEM | 380 ± 12 | .685 ± .026 | 40.8 ± .3 | 38 ± 9 | 2.51 ± .31 | | 75 ± 3 | −1.91 ± .29 |

TABLE 4

Study 3

| Vit. D Compound | 16 Day Wt. | Gain/Feed | Bone Ash Incidence | Tibial Dyschondroplasia | | | | $Ca^{47}$ | |
|---|---|---|---|---|---|---|---|---|---|
| | | | | Score | #3/No. | % N3 | % N2 + 3 | Ret. | Slope |
| none | 421 | .711$^a$ | 63 | 1.85 | 11/60 | 18 | 37 | 70$^{bc}$ | −1.01$^b$ |
| D₃ | 434 | .709$^a$ | 82 | 1.69 | 13/59 | 22 | 34 | 75$^{abc}$ | −1.13$^b$ |
| 1,25(OH)₂D₃ | 421 | .666$^b$ | 56 | 1.48 | 5/58 | 9 | 16 | 78$^{ab}$ | −.72$^{ab}$ |
| 24,25(OH)₂D₃ | 424 | .696$^{ab}$ | 78 | 2.03 | 17/59 | 29 | 53 | 67$^c$ | −.77$^{ab}$ |
| 1,24,25(OH)₂D₃ | 428 | .688$^{ab}$ | 57 | 1.58 | 6/60 | 10 | 22 | 76$^{abc}$ | −.77$^{ab}$ |
| 1OHD₃ | 423 | .661$^b$ | 42 | 1.51 | 3/60 | 5 | 17 | 75$^{abc}$ | −.95$^b$ |
| 1,25(OH)₂-26-27[²H]₆D₃ | 422 | .687$^{ab}$ | 42 | 1.30 | 0/60 | 0 | 8 | 80$^a$ | .15$^a$ |
| 1,25(OH)₂-24R-FD₃ | 413 | .663$^b$ | 60 | 1.36 | 3/60 | 5 | 15 | 72$^{abc}$ | −.47$^{ab}$ |
| Mean ± SEM | 423 ± 7 | .685 ± .013 | 59 ± 7 | 1.60 ± 15 | | 12 ± 4.5 | | 74 ± 3 | −.71 ± .31 |
| Analysis of variance probabilities: Treatment | .555 | .044 | <.001 | .019 | | <.001 | | .064 | .118 |

Study 4

| Vitamin D compound | 16 Day wt. | Gain/feed | Bone ash | Tibial dyschondroplasia | | | |
|---|---|---|---|---|---|---|---|
| | | | | Incidence | Score | % #3 | #3/total |
| None (basal diet) | 356$^{cd l}$ | .681$^{ab}$ | 35.07$^c$ | 54$^a$ | 2.30$^{ab}$ | 35$^a$ | 19/55 |
| D₃ | 383$^a$ | .701$^a$ | 35.68$^{bc}$ | 44$^{ab}$ | 2.75$^a$ | 35$^a$ | 20/58 |
| 1,25(OH)₂D₃ | 355$^{cd}$ | .652$^b$ | 36.88$^a$ | 18$^d$ | 1.58$^b$ | 8$^b$ | 4/52 |
| 24,25(OH)₂D₃ | 351$^d$ | .663$^b$ | 35.53$^{bc}$ | 53$^a$ | 2.78$^a$ | 46$^a$ | 25/56 |
| 1,24,25(OH)₂D₃ | 376$^{ab}$ | .681$^{ab}$ | 36.07$^b$ | 23$^{cd}$ | 1.89$^{ab}$ | 14$^b$ | 8/57 |
| 1OHD₃ | 372$^{abc}$ | .655$^b$ | 36.77$^a$ | 29$^{bcd}$ | 2.21$^{ab}$ | 15$^b$ | 8/57 |
| 1,25(OH)₂-26-27[²H]₆D₃ | 360$^{bcd}$ | .646$^b$ | 37.45$^a$ | 16$^d$ | 1.63$^b$ | 7$^b$ | 4/58 |
| 1,25(OH)₂-24R-FD₃ | 360$^{bcd}$ | .661$^b$ | 35.48$^{bc}$ | 41$^{abc}$ | 2.06$^{ab}$ | 16$^b$ | 9/56 |
| Mean ± SEM | 364 ± 6 | .667 ± .012 | 36.12 ± .23 | 34 ± 6 | 2.15 ± .31 | 22 ± 5 | |
| Analysis of variance probabilities: Treatment | .0059 | .0273 | .0001 | .0001 | .0605 | .0001 | |

[1]Duncan's multiple range test, values with different superscript letters are significantly different, $P \leq 0.05$.

At 16 days of age, pen body weights were obtained for all birds and their feed consumption was recorded. The birds were then killed and all birds were examined at random for tibial dyschondroplasia by making a longitudinal cut across the tibia and scoring for incidence and severity of tibial dyschondroplasia.

The method used to score the severity of the disease is described in H. Edwards and J. Veltmann, "The Role of Calcium and Phosphorus in the Etiology of Tibial Dyschondroplasia in Young Chicks", *J. Nutr.*, 113, 1568 (1983), incorporated herein by reference. Briefly, using a three week old chicken as the reference animal, a score of zero indicates normal cartilage which is narrow with little irregularities. A score of one indicates cartilage which is thickened or shows considerable irregularities. A score of two indicates that the cartilage is thickened and there is evidence of persisting prehypertrophic cartilage that is not calcified and which has not been invaded by vessels from the metaphysis. Deep irregularities are apparent. A score of three indicates a large mass of cartilage in the proximal end of the tibia.

After the tibia was scored for incidence and severity of tibial dyschondroplasia, the left tibia was removed for a bone ash determination on the fat-free dried bone.

Absorption and retention of dietary calcium was measured by orally dosing chicks with $^{47}Ca$ and then measuring the total body radioactive count, as described in Suso and Edwards, "A Study of Techniques for Measuring $^{65}Zn$ Absorption and Biological Half-life in the Chicken," *Poult. Sci.* 47:991–999 (1968). Specifically, ten 7 day old birds in one pen under the indicated dietary treatments were dosed orally with 0.5 milliliter of water solution containing 0.5 microcuries of $^{47}Ca$ and 0.1–1.0 micrograms of calcium. The total body radioactive content of the individual chickens was determined immediately following dosing, and also on day 7, 9, 12 and 14 following dosing. A plot of percent administered $^{47}Ca$ which was retained versus number of days retained yields a line which has a slope corresponding to the half-life of the radioactive calcium in the chicken, and a y-intercept that corresponds to the amount of calcium absorbed by the chicken.

Effect of 1,25-Dihydroxycholecalciferol,
1,25-Dihydroxy-26,27-hexadeuterocholecalciferol,
1-Hydroxycholecalciferol,
1,24,25-Trihydroxycholecalciferol,
1,25-Dihydroxy-24-fluorocholecalciferol, and
24,25-(OH)2-Dihydroxycholecalciferol.

In Studies 1 and 2, the effect in broiler cockerels of Vitamin D₃, 25-hydroxycholecalciferol, and 1,25-dihydroxycholecalciferol on growth, feed efficiency, bone ash, $^{47}Ca$ retention, and incidence and severity of tibial dyschondroplasia was determined. The results are shown in Table 3. The basal diet contained 1100 ICU (27.5g) vitamin D₃/kg feed. Disulfiram was added as indicated to the diets of some chickens to increase the incidence of the disease, in order to further measure the effectiveness of the compounds.

As seen in Table 3, 1,25-dihydroxycholecalciferol, in the presence or absence of disulfiram, reduced the incidence and severity of tibial dyschondroplasia over the basal diet, and increased bone ash. 25(OH)-Cholecalciferol, in the presence or absence of disulfiram, also reduced the incidence of tibial dyschondroplasia over the basal diet. Further, a diet with 1,25-(OH)2-dihydroxycholecalciferol resulted in significantly more dietary $^{47}$Ca absorbed than in a basal diet, while increasing the half life, or retention, of the calcium administered.

Table 4 illustrates the results of Studies 3 and 4, in which the effect of vitamin $D_3$ (cholecalciferol) (1), 1,25- dihydroxycholecalciferol (2), 1,25-dihydroxy-26,27-hexadeuterocholecalciferol (3), 1-hydroxycholecalciferol (4), 1,24,25-trihydroxycholecalciferol (5), 1,25-dihydroxy-24-fluorocholecalciferol (6), and 24,25-(OH)2-dihydroxycholecalciferol, on the incidence and severity of tibial dyschondroplasia, bone ash and absorption and retention of calcium was measured. The basal diet contained 1100 ICU of Vitamin $D_3$ per kg feed.

Studies 3 and 4 substantiated the results of studies 1 and 2 that administration of 10 µg/kg feed of 1,25-dihydroxycholecalciferol to the bird per day for the life of the bird substantially reduces the incidence and severity of tibial dyschondroplasia over the basal diet, and increases bone ash.

The addition of 24,25-dihydroxycholecalciferol was not effective in preventing the development of tibial dyschondroplasia.

The chickens that received feed containing 1,24,25-trihydroxycholecalciferol, 1-hydroxycholecalciferol, 1,25-dihydroxy-26,27-hexadeuterocholecalciferol and 1,25-dihydroxy-24-fluorocholecalciferol had a significant reduction in the incidence of tibial dyschondroplasia.

Preparation of Vitamin $D_3$ Derivatives

The vitamin $D_3$ derivatives of the present invention can be prepared by the following procedures.

1,25-Dihydroxycholecalciferol can be prepared as described in *Biochemistry* 10(14), 2799 (1971), and U.S. Pat. No(s). 4,310,467 and 3,697,559.

1,25-Dihydroxy-26,27-hexadeuterocholecalciferol can be prepared as described for the synthesis of 1,25-dihydroxycholecalciferol in *Tet. Let.* 40, 4147 (1972), with the substitution of a trideuteromethyl Grignard reagent in place of the methyl Grignard reagent used to add the carbons at the 26 and 27 positions.

1-Hydroxycholecalciferol can be prepared by the methods described in *J. Am. Chem. Soc.* 95(8), 2748 (1973) and U.S. Pat. No. 3,741,996.

1,24,25-Trihydroxycholecalciferol can be prepared by the method described in U.S. Pat. No. 3,847,955.

1,25-Dihydroxy-24-fluorocholecalciferol can be prepared by the procedure described in *J. Oro. Chem.* 53(5), 1040 (1988).

25-Hydroxycholecalciferol can be prepared as described in U.S. Pat. No(s). 4,310,467 and 3,565,924.

Modifications and variations of the present invention of a method and compositions to treat tibial dyschondroplasia will be obvious to those of skill in the art from the foregoing detailed description of the invention. Such modifications and variations are intended to come within the scope of the appended claims.

I claim:

1. A method for treating or preventing tibial dyschondroplasia in animals other than fowl comprising administering a composition delivering to the animal at least 1 microgram per kilogram of body weight of animal per day of a vitamin $D_3$ derivative selected from the group consisting of 1,25-dihydroxy-26,27-hexadeuterocholecalciferol, 1,24,25-trihydroxycholecalciferol, 1,25-dihydroxy-24-fluorocholecalciferol and mixtures thereof, in combination with a pharmaceutically acceptable carrier selected from the group consisting of pharmaceutical carriers suitable for injection by intraperitoneal administration and intramuscular administration, controlled delivery devices, and carriers for oral ingestion.

2. The method of claim 1 further comprising administering to the animal vitamin $D_3$ in combination with an effective amount of the vitamin $D_3$ derivative.

3. The method of claim 1 wherein the carrier is suitable for injection, administering the composition intraperitoneally.

4. The method of claim 1 further comprising administering the composition in a pharmaceutically acceptable carrier selected from the group consisting of saline, phosphate buffered saline, and propylene glycol.

5. The method of claim 1 further comprising administering the composition in a feed.

6. The method of claim 5 which delivers a dosage of between approximately 5 and 20 micrograms of vitamin $D_3$ derivative per kilogram of feed.

7. The method of claim 1 further comprising administering the composition in a biocompatible controlled delivery device selected from the group consisting of delayed slow release boluses, microspheres, microcapsules, orally administerable biodegradable capsules, and biodegradable implants.

8. The method of claim 1, wherein the administration of the vitamin $D_3$ derivative is initiated on the first day of life.

9. The method of claim 1, wherein the vitamin $D_3$ derivative is administered during the rapid growth phase of the animal.

10. The method of claim 1, wherein the vitamin $D_3$ derivative is administered for the life of the animal.

11. A method of treating or preventing tibial dyschondroplasia in fowl comprising administering to the fowl a composition between 0.1 and 20 micrograms per kilogram of body weight per day of a vitamin $D_3$ derivative selected from the group consisting of 1,25-dihydroxy-26,27-hexadeuterocholecalciferol, 1,24,25-trihydroxycholecalciferol, 1,25-dihydroxy-24-fluorocholecalciferol and mixtures thereof, in combination with a pharmaceutically acceptable carrier selected from the group consisting of pharmaceutical carriers suitable for injection by intraperitoneal administration and intramuscular administration, controlled delivery devices, and carriers for oral ingestion.

12. The method of claim 11, wherein the vitamin $D_3$ derivative is administered for the first three weeks of life.

13. The method of claim 11 further comprising administering to the fowl vitamin $D_3$ in combination with an effective amount of the vitamin $D_3$ derivative.

14. The method of claim 11, wherein the carrier is a feed comprising between approximately 5 and 20 micrograms of vitamin $D_3$ derivative per kilogram of feed.

15. The method of claim 11 further comprising administering the composition in a controlled delivery device selected from the group consisting of a time or slow release bolus, a microsphere, a microcapsule, an orally administered capsule that can be time released, and a biodegradable, biocompatible implant.

16. The method of claim 11, wherein the vitamin $D_3$ derivative is initiated on the first day of life.

17. The method of claim 11, wherein the vitamin $D_3$ derivative is administered during the rapid growth phase of the fowl.

18. The method of claim 11, wherein the vitamin $D_3$ derivative is administered for the first three weeks of life.

19. The method of claim 11, wherein the vitamin $D_3$ derivative is administered for the life of the fowl.

* * * * *